(12) United States Patent
Marbach

(10) Patent No.: US 11,099,123 B2
(45) Date of Patent: Aug. 24, 2021

(54) METHOD FOR CALIBRATING AN INTEGRATING CAVITY

(71) Applicant: GrainSense Oy, Oulu (FI)

(72) Inventor: Ralf Marbach, Oulu (FI)

(73) Assignee: GrainSense Oy, Oulu (FI)

( * ) Notice: Subject to any disclaimer, the term of this patent is extended or adjusted under 35 U.S.C. 154(b) by 0 days.

(21) Appl. No.: 16/964,721

(22) PCT Filed: Jan. 29, 2019

(86) PCT No.: PCT/FI2019/050061
§ 371 (c)(1),
(2) Date: Jul. 24, 2020

(87) PCT Pub. No.: WO2019/149997
PCT Pub. Date: Aug. 8, 2019

(65) Prior Publication Data
US 2020/0355603 A1 Nov. 12, 2020

(30) Foreign Application Priority Data
Jan. 30, 2018 (FI) .................................. 20185082

(51) Int. Cl.
*G01N 21/27* (2006.01)
*G01N 33/00* (2006.01)

(52) U.S. Cl.
CPC ....... *G01N 21/274* (2013.01); *G01N 33/0098* (2013.01); *G01N 2201/065* (2013.01); *G01N 2201/12723* (2013.01)

(58) Field of Classification Search
CPC ............... G01N 21/274; G01N 21/278; G01N 2201/065; G01N 2201/127
See application file for complete search history.

(56) References Cited

U.S. PATENT DOCUMENTS

| 4,575,252 A | 3/1986 | Akiyama |
| 5,422,485 A | 6/1995 | Bowlds |

(Continued)

FOREIGN PATENT DOCUMENTS

| EP | 0209247 A1 | 1/1987 |
| EP | 2315003 A1 | 4/2011 |

(Continued)

OTHER PUBLICATIONS

Elterman: Integrating Cavity Spectroscopy. Applied Optics. vol. 9, No. 9, p. 2140.

(Continued)

*Primary Examiner* — Maurice C Smith
(74) *Attorney, Agent, or Firm* — Laine IP Oy

(57) ABSTRACT

In accordance with an example aspect of the present invention, there is provided a method of obtaining a calibrated measurement of a sample using an integrating cavity, comprising obtaining sample spectral information by using the integrating cavity with the sample placed inside the integrating cavity, obtaining cavity-characterizing spectral information generated by using the integrating cavity with a standard object, and obtaining a measurement result from the sample spectral information by employing a mathematical process that takes the cavity-characterizing spectral information as input.

13 Claims, 3 Drawing Sheets

(56) References Cited

U.S. PATENT DOCUMENTS

| | | | |
|---|---|---|---|
| 5,956,133 A * | 9/1999 | Imura | G01N 21/474 |
| | | | 356/236 |
| 2003/0023152 A1 | 1/2003 | Abbink et al. | |
| 2005/0134853 A1 * | 6/2005 | Ingleson | G01N 21/255 |
| | | | 356/402 |
| 2008/0204705 A1 | 8/2008 | Liu | |
| 2010/0243876 A1 | 9/2010 | Resch-Genger et al. | |
| 2010/0277727 A1 | 11/2010 | Schlaminger | |
| 2011/0128540 A1 | 6/2011 | Iida et al. | |
| 2016/0299062 A1 | 10/2016 | Marbach | |
| 2017/0010214 A1 | 1/2017 | Osawa et al. | |
| 2017/0059481 A1 | 3/2017 | Tixier | |
| 2017/0088941 A1 * | 3/2017 | Schroeder | G01N 21/93 |
| 2019/0182440 A1 * | 6/2019 | Xin | G01J 3/10 |

FOREIGN PATENT DOCUMENTS

| | | |
|---|---|---|
| EP | 3141887 A1 | 3/2017 |
| EP | 3211400 A1 | 8/2017 |
| JP | H10160570 A | 6/1998 |
| WO | WO2014080322 A1 | 5/2014 |

OTHER PUBLICATIONS

Hanssen et al: Integrating Spheres for Mid- and Near-infrared Reflection Spectroscopy. Handbook of Vibrational Spectroscopy, 2002. XP055276994. URL:http://www.nist.gov/calibrations/upload/HndBkSphere.pdf.

Krochmann et al: Practical Methods for the Measurement of Reflectance and Transmittance. CIE 130-1998.

* cited by examiner

```
┌─────────────────────────────────────┐
│ Obtaining sample spectral information│──110
│ by using an integrating cavity with a│
│ sample placed inside the integrating │
│ cavity                               │
└─────────────────────────────────────┘
                  │
                  ▼
┌─────────────────────────────────────┐
│ Obtaining cavity-characterizing     │──120
│ spectral information generated by    │
│ using the integrating cavity with a  │
│ standard object                      │
└─────────────────────────────────────┘
                  │
                  ▼
┌─────────────────────────────────────┐
│ Obtaining a measurement result from │──130
│ the sample spectral information by   │
│ employing a mathematical process that│
│ takes the cavity-characterizing      │
│ spectral information as input        │
└─────────────────────────────────────┘
                  │
                  ▼
┌─ ─ ─ ─ ─ ─ ─ ─ ─ ─ ─ ─ ─ ─ ─ ─ ─ ─ ┐
  Comparing second cavity-characterizing
│ spectral information to the cavity- │──140
  characterizing spectral information, and
│ responsive to the comparison indicating the│
  second cavity-characterizing spectral
│ information differs from the cavity-│
  characterizing spectral information, using the
│ second cavity-characterizing spectral│
  information in obtaining the measurement
│ result                              │
└─ ─ ─ ─ ─ ─ ─ ─ ─ ─ ─ ─ ─ ─ ─ ─ ─ ─ ┘
```

Fig. 1

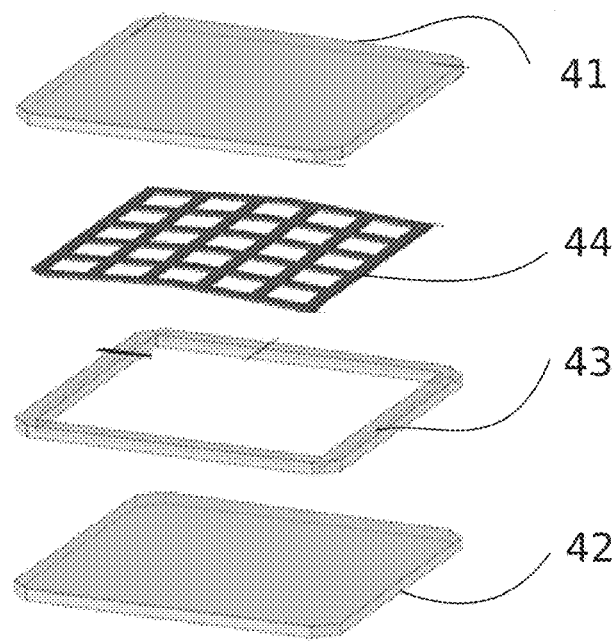
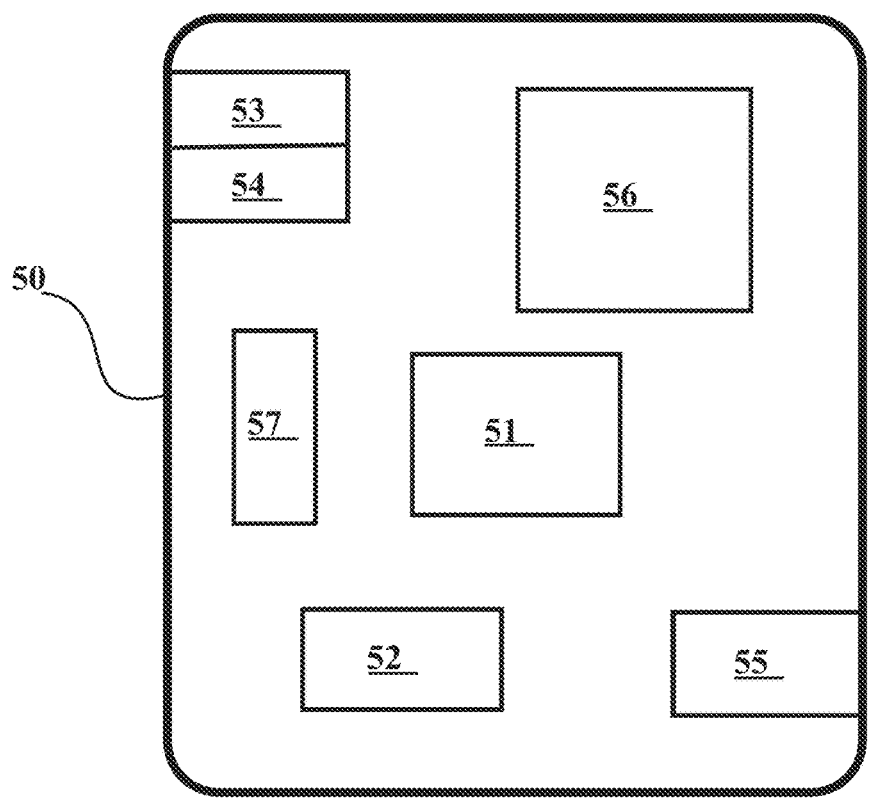
Fig. 4
Fig. 5

METHOD FOR CALIBRATING AN INTEGRATING CAVITY

FIELD OF THE INVENTION

The invention relates to methods and devices for calibrating integrating cavities, for example for spectroscopic use.

BACKGROUND OF THE INVENTION

Many properties of a sample can be measured in an integrating cavity, see e.g. the standard of CIE 130-1998 "Practical Methods for the Measurement of Reflectance and Transmittance", where e.g. measurement of reflectance for directional and hemispherical incidence of radiation, diffuse reflectance, transmittance for directional and hemispherical incidence of radiation, and diffuse transmittance are addressed. Integrating cavities can also be used in analytics, such as in spectrophotometers for spectroscopic measurements of samples, see e.g. WO 2104/080322. If a radiant flux is introduced into an integrating cavity, e.g., a sphere, through a small entrance aperture, then, because of the diffuse nature of the reflections at the sphere wall, the optical power distribution inside the cavity will quickly, i.e., after a few bounces, become uniform and isotropic. When a fraction of that diffuse, that is, uniform and isotropic, optical power escapes from the cavity through an opening in the wall, known as an exit port, then the distribution of the escaping optical rays is Lambertian with respect to the plane of the opening. In a spherical cavity filled with ideally diffuse radiation, radiation reflected from any one point on the wall will irradiate all other points on the surface equally. Spherical or near-spherical shapes are therefore often preferred in praxis, because then the mixing happens with a minimum number of bounces.

When an absorbing sample is put inside an integrating cavity, the power density of the diffuse field inside the cavity decreases. This decrease can be measured with a photodetector, which can be located inside the cavity, or, more commonly, outside the cavity and "looking" at an exit port. An absorbance-like spectrum of the sample can be measured in the same way as in the case of a conventional transmission cuvette, namely, by dividing the detector intensity measured with the sample inside the cavity, $H_{sample}(\lambda)$, where $\lambda$ the optical wavelength, with the detector intensity measured with a reference object inside the cavity, $H_{ref}(\lambda)$, which usually is just the empty sphere, that is, just air inside. For example, when using the decadic logarithm, the absorbance spectrum is, $A(\lambda)=-\log_{10}(H_{sample}(\lambda)/H_{ref}(\lambda))$. The method of measuring samples inside the integrating cavity is particularly useful for samples having a low absorption coefficient, as the effective absorbance pathlength is amplified by the multiple sample interactions of the diffuse light inside the cavity and the measurement result is virtually independent of changes in the geometry of the sample, scattering within the sample, and reflections at the surface of the sample.

SUMMARY OF THE INVENTION

In accordance with a first aspect of the present invention, there is provided a method of obtaining a calibrated measurement of a sample using an integrating cavity, comprising obtaining sample spectral information by using the integrating cavity with the sample placed inside the integrating cavity, obtaining cavity-characterizing spectral information generated by using the integrating cavity with a standard object, and obtaining a measurement result from the sample spectral information by employing a mathematical process that takes the cavity-characterizing spectral information as input.

Various embodiments of the first aspect may comprise at least one feature from the following bulleted list:
- the cavity-characterizing spectral information is obtained by using the integrating cavity with the standard object placed inside the integrating cavity
- the cavity-characterizing spectral information is obtained by using the integrating cavity with the standard object replacing part of an inner surface of the integrating cavity
- the method further comprises obtaining a second cavity-characterizing spectral information and comparing it to the cavity-characterizing spectral information, and responsive to the comparison indicating the second cavity-characterizing spectral information differs from the cavity-characterizing spectral information, using the second cavity-characterizing spectral information in obtaining the measurement result
- the sample comprises at least one of a solid sample, a liquid sample and a gaseous sample
- the sample comprises a solid sample, the sample comprising at least one plant seed
- the standard object comprises an object with an optically black layer thereon
- the object has at least one hole penetrating the optically black layer
- the object is encased in glass
- the glass comprises fused silica or borosilicate glass
- the glass is glass welded to enclose the object
- the standard object comprises a volume of absorbing material, amounting to volume absorber In accordance with a second aspect of the present invention, there is provided a standard object, comprising a metallic object with an optically black layer thereon, and a transparent enclosure encasing the metallic object and optically black layer.

Various embodiments of the second aspect may comprise at least one feature from the following bulleted list:
- the metallic object further has at least one hole penetrating the optically black layer
- the metallic object has a plurality of holes penetrating the optically black layer
- the transparent enclosure comprises fused silica or borosilicate glass
- the transparent enclosure is at least one of glass welded, fused and glued to enclose the metallic object.

In accordance with a third aspect of the present invention, there is provided a standard object, comprising a volume of absorbing material, amounting to a volume absorber, and wherein the volume of absorbing material has been constructed to have a specific pre-defined absorbance cross section.

BRIEF DESCRIPTION OF THE DRAWINGS

FIG. 1 is a workflow scheme of the inventive method for correcting an absorbance spectrum;

FIG. 4 shows an embodiment of a standard object according to the present invention; and FIG. 5 shows an example of a computer system to be used in the present invention.

DETAILED DESCRIPTION OF EMBODIMENTS

Figure 2:
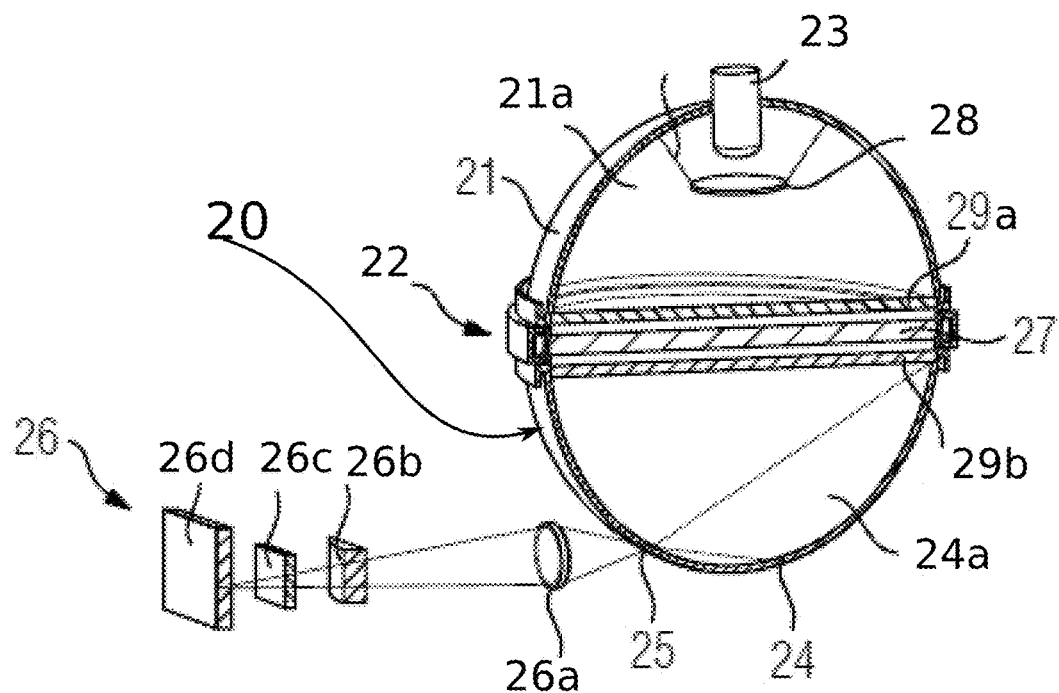
FIG. 2 shows in cross-section a schematic setup of an optical analyzer with an optically integrating cavity.

One disadvantage of using an integrating cavity with the sample inside the cavity will arise from the way the measurement of the reference spectrum, $H_{ref}(\lambda)$, is performed. Unlike cases where the sample is located outside the integrating cavity, that is, diffuse reflection or diffuse transmission geometries, the optical characteristics of the cavity must be long-term stable when the cavity is used with the sample inside the cavity. The reason is as follows. Drift phenomena in the emission of light source(s), sensitivity of detector(s), and transmission factors or other efficiency factors of any optics outside of the sphere always cancel out of the spectroscopic reference ratio, $H_{sample}/H_{ref}$, regardless of the position of the sample. However, the transmission factor of the sphere itself only cancels out from the reference ratio when the sample is located outside the sphere.

The present disclosure relates to apparatus and methods for controlling the effects of drift in the optical properties of an integrating cavity from the resulting absorbance spectra, or absorbance like spectra, in cases where the sample is located inside the sphere. The disclosed standardization measurement improves spectroscopic referencing. The spectroscopic reference ratio, $H_{sample}/H_{ref}$, eliminates drifts originating from components outside the sphere, including short-term drifts of the lamp and detector. The reference spectrum, $H_{ref}(\lambda)$, may therefore be re-measured fairly frequently, typically every few minutes and usually at least once per day. The disclosed sphere standardization method, on the other hand, becomes necessary only when the sphere's optical properties have changed, which is typically less frequently. If a sphere is used very carefully, such as in a laboratory, its properties may not change for years. However, even in this case, it is desirable for the laboratory to have, for example, a second sphere available for backup. The disclosed standardization method is useful also in this situation, because after the two spheres have been standardized to the laboratory's own long-term stable standard object, the spheres behave identically with regard to measuring absorbance or other absorbance-like spectra, and therefore can be swapped quickly when necessary, that is, without the need to re-calibrate the set-up. In other words, easy calibration transfer is achieved.

Many sphere applications are based on precision spectroscopic measurements, for example, when small absorbance bands need to be measured that are overlapped by larger, varying amounts of absorbance from other components in the sample. This situation is known as matrix absorbance. In these and other precision applications, and especially when chemometric models are needed for quantitative analysis, the disclosed method can advantageously be used to maintain the analytical accuracy of the cavity measurement system. Chemometric models may be developed using the spectra of a "young" cavity. Subsequent drifts in the optical response may produce error and degrade the original accuracy of the sphere over time. A number of physical effects contribute to sphere aging and behavior, including temperature sensitivity, ultraviolet (UV) light sensitivity, mold sensitivity, moisture sensitivity, dirt build-up, aging of paints, mechanical damage to corners and edges, scratches on surfaces and windows, and/or any other long-term chemical or physical changes in the quality of the white diffusive material.

Thus, a simple and accurate method to standardize the optical response of an integrating cavity is needed.

The present invention facilitates improvement of the quality of spectral information obtained with samples inside an integrating cavity, such as for example an integrating sphere. A simple and accurate way to standardize the optical response of an integrating cavity is provided. The spectral information, such as for example absorbance spectra, may be rendered absolute in scale, enabling obtaining of virtually identical absorbance spectra from any given sample with different integrating cavities.

The advantages of the invention include the use of scaled spectra rather than original measured spectra. A chemometric model may be developed based on scaled spectra, which will maintain its analytical accuracy longer, theoretically even for an unlimited time, because the effect of "sphere aging" may be attenuated, even eliminated. Another important advantage is the ability to develop a chemometric model on one sphere and then transfer it to other spheres, because differences between the individual spheres may be eliminated in the scaled spectra, as the scaled spectra are referenced, so to speak, to a standard object and not to an empty sphere, as the original spectra. A similar advantage applies in cases where intentional changes are made to a sphere.

An integrating cavity that can be used to measure optical properties of samples placed in the cavity can be of any shape, at least in principle. However, spheres or near-spherical shapes are advantageous because their diffusing effect is strongest, that is, fewer reflections inside the cavity are needed to uniformly distribute the incoming rays across the surface than in other shapes. In the following embodiments described, the described integrating cavities are spherical, but the invention is not limited to any particular shape of cavity.

With a sample located inside a hollow cavity having small holes for light entrance and exit ports, the measurement results are dependent on the optical properties of the cavity. When the interior surface of the cavity is covered with a diffuse white reflective coating, it becomes a so-called integrating cavity. The diffuse white coating approximates a so-called Lambertian reflector, which means light rays incident on the inner surface are diffusely reflected and, subsequent to a few reflections, lose information concerning their original direction of arrival. After one or few such diffuse reflections, the light rays are distributed equally across the whole surface. Thus, the original direction of the light is "forgotten" by the diffusing effect inside the integrating cavity.

From spectral information of a sample measured inside an integrating sphere, the chemical composition of the sample may be determined, for example. Spectral information may comprise, for example, an absorbance spectrum, or absorbance values at selected wavelength points.

More frequently in the field, samples to be analyzed are placed outside an integrating sphere, for example to cover a port machined into a wall of the sphere. However, advantages of placing the sample inside the integrating cavity include:
  amplification of the absorbance signal due to a sphere multiplier factor
  virtual elimination of sample presentation errors
  simplicity of loading samples, also granular and liquid samples
  high detector irradiance levels
  small dynamic range for the photodetector and electronics, and ease of achieving a linear and reliable absorbance response from the sample.

The surfaces of modern spheres are covered with, or made from, materials with very high diffuse reflection, typically $\rho > 0.95$. Modern materials also are spectrally non-selective (weak dependence on wavelength), non-fluorescent, and long-term stable. Still, especially during harsh use conditions, changes to a sphere's optical characteristics will occur in the long run. Most spheres used in practice have diameters in the range from about 50 millimeter to 1 meter. The apertures for light sources and detectors are called ports, wherein the total area of all ports is typically less than 5% of the surface area of the sphere.

When using an integrating sphere with the sample placed outside the sphere, that is, when measuring diffuse reflection or diffuse transmission properties, aging effects of the sphere cancel themselves out in the spectroscopic reference ratio when measurement results are obtained. In other words, the fact that optical or spectral characteristics of the sphere change over time is not a problem in cases when the sample is outside the sphere.

The cancelling out of the aging effects of the sphere does not occur when the sample to be analyzed is inside the sphere. Performing a spectroscopic reference measurement with the sample replaced by air, that is, removed from the sphere, does not work the same way as in the case where the sample to be analyzed was outside the sphere when measured. For example, when measuring an absorbance spectrum, $A = -\log_{10}(H_{sample}/H_{ref})$, drifts in the optical properties of the sphere do not cancel out, because changes in the optical properties of the sphere result in effects that are mathematically roughly similar to pathlength changes in the case of conventional cuvette transmission spectroscopy.

Since the aging effects do not cancel out, controlling them becomes important when integrating spheres are used in a mode where the sample to be analyzed is inside the sphere. By being inside the sphere, or more generally an integrating cavity, it is meant the sample is completely inside the cavity. Alternatively, the sample may be inside the cavity in the sense that more than half of a volume of the sample is inside the cavity. While paint aging, accumulation of dust and other effects may be subtle, certain measurements, in order to be successful, require stability in the order of 0.01% over time. For example, some near-infrared analytical measurements fall into this category, where small analyte peaks need to be subtracted from a large and varying background. A useful life of an integrating sphere may be several years, which in turn means that changes large enough to significantly affect the accuracy of measurement will likely occur during the lifetime of the sphere.

According to the invention, a standard object, or standard, with good long-term stability of its optical properties may be used to both detect and correct changes in the characteristics of an integrating sphere.

A standard having a stable absorbance cross-section, for example, is made available and measured in the sphere at the time of sphere assembly to obtain cavity-characterizing spectral information that characterizes the sphere at time of assembly. The cavity-characterizing spectral information may be used in connection with measuring samples using the sphere, to cast spectral information obtained from the samples against the standard object, rather than against an empty sphere. Since the standard object is stable, unlike the empty sphere, the samples are thereby stably measured and aging effects of the sphere may be substantially mitigated.

As time goes by, a new measurement of the same standard, or another but nominally identical standard, may be performed with the same sphere to obtain new cavity-characterizing spectral information. In case the new cavity-characterizing spectral information differs from the earlier information, the new cavity-characterizing spectral information may be used in connection with measuring samples thereafter, since the new cavity-characterizing spectral information now more accurately reflects the state of the sphere. In this case, the new cavity-characterizing spectral information may then be used to cast spectral information obtained from samples against the standard object and the age-related changes in the sphere itself may be removed, or at least significantly attenuated, enabling improved measurement accuracy.

For example, when working with absorbance spectra, $-\log_{10}(H_{sample}/H_{ref})$, the standardization method can be performed as follows. First, the absorbance spectrum of the standard object, $A_{std}(\lambda) = -\log_{10}(H_{std}(\lambda)/H_{ref,std}(\lambda))$, is measured and saved to memory. Next, routine measurements of absorbance spectra of one or more samples can start, $A(\lambda) = -\log_{10}(H_{sample}(\lambda)/H_{ref}(\lambda))$. In general, the reference spectra of the samples, $H_{ref}(\lambda)$, can in principle be identical to the reference spectrum, $H_{ref,std}(\lambda)$, that was used for computing the absorbance spectrum of the standard, but more usually new, or fresh, reference spectra will be measured. Third, divide the absorbance spectrum of the sample, $A(\lambda)$, by the absorbance spectrum of the standard object, $A_{std}(\lambda)$, to obtain the sample's standardized absorbance spectrum, $A_n(\lambda) = A(\lambda)/A_{std}(\lambda)$. As in the case of the other spectral ratios, for example, $H_{sample}(\lambda) H_{ref}(\lambda)$, the division sign in the equation is equivalent to the "./" notation in the MATLAB software by Mathworks, that is, the divisions are made point-by-point separately at each wavelength. In the case of spectroscopic measurements, the variables may be measured at several wavelength bands and therefore saved to memory as vectors, rather than scalars. Performing quantitative analysis on the standardized spectra, $A_n(\lambda)$, will result in better reliability and long-term stability of the analytical results, because drift in the sphere's optical properties can be countered by simply measuring a fresh absorbance spectrum of the standard, storing it, and using it for standardizing the sample spectra. This is much simpler than today's practice of re-calibrating the whole set-up. The only requirement is that the optical properties of the standard object itself are long-term stable.

The procedure works not only with absorbance spectra, $A(\lambda) = -\log_{10}(H_{sample}(\lambda) H_{ref}(\lambda))$, but also with other absorbance-like spectra that are based on the ratio, $H_{sample}/H_{ref}$. To shorten notation, it is possible to drop the $\lambda$ in the equations. Dividing by the standard's absorbance-like spectrum facilitates restoring analytical stability.

For normal absorbance spectra, $-\log_{10}(\ldots)$, which use the decadic logarithm and where the numerical output is quoted in so-called absorbance units, AU, the correction works extremely well for small absorbance values, namely, up to about 0.3 AU, and fairly well also for larger absorbance values.

Alternatively, the natural logarithm can be used, $A_e = -\log_e(H_{sample}/H_{ref})$, in which case the same statement as above applies, except that now the numerical range over which the correction works extremely well reaches up to about 0.7, that is, 0.3×2.303.

The first-order Taylor-series approximation of absorbance $A_e$ is, $A_1 = ((H_{ref}/H_{sample}) - 1)$. Surprisingly, the correction method was found to work extremely well with $A_1(\lambda)$ spectra. In other words, the normalization procedure, $A_1(\lambda)/A_{1,STD}(\lambda)$, corrects drifts in the sphere extremely well over a wide dynamic range of $A_1$.

All absorbance-like formulas work well over some range. In praxis, it is thus possible to find a formula that is both good for quantitative analysis, i.e., Lambert-Beer like behavior of the samples, and good for sphere correction.

Note that the correction effect described above is not due to a "double ratio" effect, because the two involved spectral ratios, $H_{Sample}(t)/H_{Ref}(t)$ and $H_{Std}(t_1)/H_{Ref}(t_1)$, where t is time, are not directly divided by each other. The correction effect is also not due to a simple pathlength correction. If this were the case, the correction would work best on normal absorbance spectra, $A = -\log_{10}(\ldots)$, which is not the case, because the correction works best on $A_1$ spectra, $A_1 = ((H_{ref}/H_{sample}) - 1)$. Rather, the stabilization effect afforded by dividing an absorbance or absorbance-like spectrum of the sample with a similar or even different absorbance-like spectrum of a long-term stable standard, is a fortunate result of the physical intricacies how integrating spheres behave when used with the sample located inside the sphere.

The standard object may comprise, for example, a strip of metal or plastic, upon or in which is an optically black layer. By optically black it is herein meant that it absorbs virtually all incoming light. The optically black layer may be inorganic, for example. An example material for the optically black layer is so-called "black nickel", which is a commercially available coating for metals. Due to the electroless deposition process, the layer grows uniformly also on edges and inside-corners of the work piece. Multiple other materials can be used to make optically black layers, including various paints and surface treatments. Overviews can be found, e.g., in the following two papers: (a) Stephen M. Pompea and Robert P. Breault, CHARACTERIZATION AND USE OF BLACK SURFACES FOR OPTICAL SYSTEMS, Chapter 6 in Handbook of Optics, Third Edition Volume IV: Optical Properties of Materials, Nonlinear Optics, Quantum Optics. M. Bass (ed.), McGraw-Hill, 2010; and (b) Jennifer L. Marshall, Patrick Williams, Jean-Philippe Rheault, Travis Prochaska, Richard D. Allen, D. L. DePoy, CHARACTERIZATION OF THE REFLECTIVITY OF VARIOUS BLACK MATERIALS, Jul. 30, 2014 (8 pp). Published in Proc. SPIE Int. Soc. Opt. Eng. 9147 (2014) 91474F.

Alternatively to a black layer, also known as a surface absorber, a standard object may comprise a volume of absorbing material, in effect amounting to a so-called volume absorber. There is no clear-cut difference between surface absorbers and volume absorbers, but the materials used inside the so-called volume absorbers typically have much lower absorption coefficients than the materials used in surface absorbers. Examples of materials well suited to realize a standard object in the form of a volume absorber include light-absorbing plastics, especially grey-colored plastics, where the total mass may be used to determine the resulting absorbance cross section and the shape may be optimized because injection molding is available as a manufacturing process. Another example of a suitable volume absorbing material is a graphite-bearing powder mix, especially mixes with non-absorbing powders like glass or Teflon particles so that the graphite is the only absorber and the mixing ratio can be used to adjust the desired degree of absorbance. The powder mix may be encased, e.g., in glass as described below. A volume absorber may be built to a specific, pre-defined absorbance cross section.

The standard object may be encased in glass to enhance its stability and enable easy cleaning to remove fingerprints and other dirt that might otherwise accumulate on the standard. The glass material may comprise fused silica, since fused silica is transparent to ultraviolet and longer near-infrared radiation, which might be absorbed by other glass types. Borosilicate glass may alternatively be used, depending on the application. Glass welding, recently available, may be used to encase the standard into the glass. Glass fusing may also be used instead of glass welding to encase the standard object into glass. In the case of a standard based on surface absorbance, at least the area of the black layer that is exposed to the light should be protected by glass, whereas other parts of the body are less critical to protect.

The standard may comprise one or more holes. The holes may be in the metal or plastic object. The hole or holes may penetrate the optically black layer. By penetrating the optically black layer it may also be meant the optically black layer covers the inside edges of the hole or holes, such that the hole or holes penetrate the metal or plastic object before the optically black layer is applied.

A benefit of the hole or holes is that, when the standard is put inside the sphere, the risk of affecting the diffuse characteristic of the optical field inside the sphere is minimized. In other words, the potential for shadowing effects is minimized. This is advantageous because the absorbance effect caused by the standard object should ideally be completely independent of its location in the sphere, which is achieved when there are no shadowing effects. In some embodiments, there are at least two holes. In further embodiments, the holes cover more than 50% of the surface of the standard object.

From practical experience and with regard to the overall resulting accuracy and the efficient use of measurement time, it is advantageous if the absorbance cross section of the standard object is selected such that the diffuse photon density building up inside the sphere is reduced to about half when the standard is put inside the sphere. In other words, and more specifically, the values of the ratio, $H_{std}(\lambda)/H_{ref,std}(\lambda)$, may preferably be in the range from about 0.4 to 0.7 over the whole wavelength range of the measurement.

FIG. 1 is a workflow scheme of at least some embodiments of the inventive method for correcting the absorbance spectra measured from a sample. An integrating cavity like the one shown in FIG. 2, having an inner surface with an essentially diffuse reflectance and a radiation source for introducing radiant power into the cavity and a detector that is sensitive to the radiant power, are assumed in place.

Phase 110 comprises obtaining sample spectral information by using the integrating cavity with the sample placed inside the integrating cavity. Sample spectral information may comprise spectral information of the sample. Phase 120 comprises obtaining cavity-characterizing spectral information generated by using the integrating cavity with a standard object. When generating the cavity-characterizing spectral information, the standard object may be inside the cavity, or it may be arranged to partly replace a wall of the cavity without being inside the cavity. Obtaining the cavity-characterizing spectral information may comprise fetching the cavity-characterizing spectral information from a memory, for example. Phase 130 comprises obtaining a measurement result from the sample spectral information by employing a mathematical process that takes the cavity-characterizing spectral information as input. Optional phase 140 comprises comparing a second cavity-characterizing spectral information to the cavity-characterizing spectral information, and responsive to the comparison indicating the second cavity-characterizing spectral information differs from the cavity-characterizing spectral information, using the second cavity-characterizing spectral information in obtaining the measurement result. The second cavity-characterizing spectral information may be generated, like the cavity-characterizing spectral information, with the standard object in the cavity. The second cavity-characterizing spectral information may be more recent than the cavity-characterizing spectral information.

FIG. 2 illustrates an example optical analyser with an integrating sphere. The sample is held in place by a sample holder. In the case of grain seeds or other particulate material, the sample holder may consist of glass 27. On glass 27, grains or other agricultural particles, for example, are kept in place and distributed across the surface to form an optically thin layer. By optically thin it is meant the sample is predominantly transparent to the diffuse light inside the integrating cavity. Also a standard object like the one in FIG. 4 may be placed between glass plates 29a, 29b.

Standard objects for spheres may be used inside handheld or on-line optical instruments. In case of handheld devices, they may be inserted and removed manually. In case of on-line instruments, the standard object may be operated automatically and may be permanently located on or inside the instrument.

FIG. 2 shows in cross-section a schematic setup of an optical analyzer with an optically integrating cavity 20 being formed by two half-spheres 21,24, which can be connected to each other using a bayonet closure, for example. A sample holder 27 can be fixed to a device housing (not shown) or to the lower half-sphere 24. The optically integrating cavity may be opened and closed using a frame 22, which establishes a form fit to at least one of the half-spheres 21,24. The frame 22 can be made of plastic or metal materials as long as their diffuse reflection is high enough not to hamper the integration ability of the optically integrating cavity 20. An optional protection glass 29a is used to protect the inner part of the upper half-sphere 21 including the front part of the light source 23, which sticks out of the half-sphere to be easily replaceable, since the protection glass 29a may be non-removable. Likewise, an optional second protection glass 29b protects the white diffusing wall 24a of the lower half-sphere 24 for optimal light homogenization.

Incoming light from the light source 23 is reflected by a baffle 28 to hit the diffusing inner wall 21a of the upper sphere half 21 and to diffuse into the integrating sphere. The sample holder 27 may be removable from the sphere 20, and may be filled with samples while in place or be taken out for the purpose. The sample holder 27 may as such accommodate also a standard object (see FIG. 4), that can be slid into the holder, for example. The frame 22 may be designed to hold the sample holder 27 tightly together with both half-spheres 21, 24, and may be permanently connected to the sample holder 27.

Through the opening 25 in the lower half-sphere 24 diffuse light may exit and be directed to a spectral sensor 26. The sensor may include some beam guiding elements, such as lenses 26a, 26b to a linear variable bandpass filter 26c and finally to a detector array 26d. Every pixel of the detector array, for example with a row of 256 pixels, corresponds to a certain wavelength of interest whereas the filter 26c takes care of transmitting the correct wavelength onto the corresponding pixel. The linear variable optical filter 26c may be replaced by a grating or a prism, and the spectral sensor 26 as a whole may be replaced by other spectrographic sensors.

Figure 3:
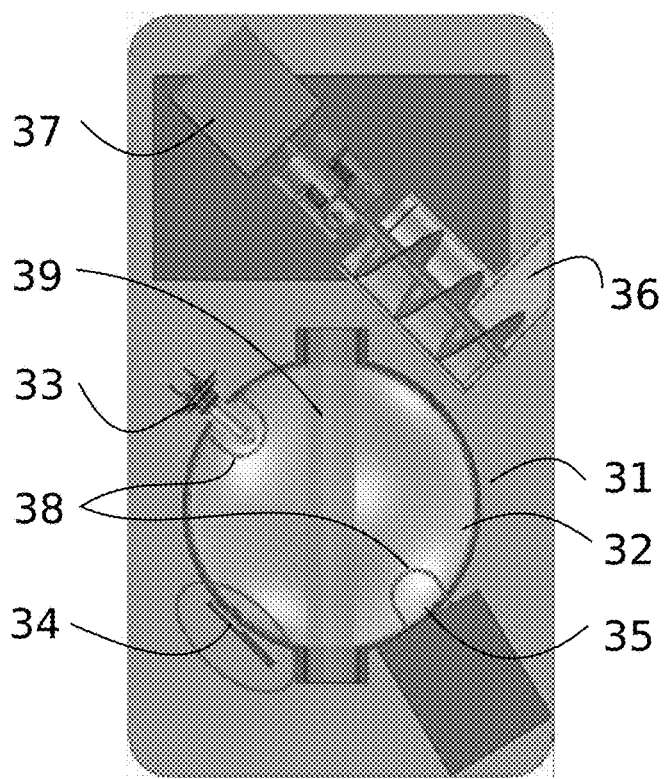
FIG. 3 shows schematically an integrating sphere with an automatically operated standard object.

FIG. 3 shows schematically an integrating sphere 31 with automatically operated standard object 34. According to some embodiments, a standard 34 which is has a diffuse white coated area and an optically black coated area is used. The black coated area realizes the standard object. In the case of very dark black coatings with, say, diffuse reflectivity<5%, the absorbance cross section of the standard is almost identical to the geometrical area of the exposed black coating. The integrating sphere 31 has a light bulb 33 and a spectrograph detector 35, both provided with baffles 38, and is used to analyse a sample stream, for example a stream of grains, that falls through a sample holder, that is, a glass tube 39 through the sphere 31.

A transport screw 36 driven by an electric motor 37 provides a continuous stream of samples to the sphere. The automatic standard 34 is located behind an opening in the wall of the sphere. The opening is either covered by a white surface, effectively "filling the opening", or is covered by a black surface realizing the standard. Mechanically, there is only one moving part, a disc or sheet having at least one white and one black field. Most of the time, the opening is covered by the white surface. A mechanical actuator (not shown) moves the dark surface over the opening, i.e., exposes the standard object, only during the short times when a new standard measurement, $H_{Std}(\lambda)$, is taken.

Spectroscopic reference measurements of the empty sphere may be made by stopping the transport screw 36, so that the stream stops. Once the stream has stopped and the sphere has become empty, two measurements may be performed, one being the empty sphere for the spectroscopic reference, $H_{Ref}(\lambda)$, and the other being the standard measurement with the black standard exposed, $H_{Std}(\lambda)$. The closeness in time between the two measurements facilitates detection of small drifts in the sphere properties.

An automatically deployed standard object may be implemented in different mechanical ways than described above, for example as follows: firstly, a black standard may move in and out through a narrow slit in the wall of the sphere. Secondly, a black area may be stationarily located in the wall of the sphere. A movable white diffuse reflector material may cover the black area, making it appear white, and can move away to expose the black area. The movable white reflector material, when moved away, may park on a neighbouring white area so that the sphere sees no change in its total amount of white area.

In FIG. 4 is shown an embodiment of a standard object to be used in systems operating in accordance with principles of the present invention. The standard object of FIG. 4 comprises a transparent glass cover sheet 41, a transparent glass bottom sheet 42 and a transparent glass frame 43 between said cover and bottom sheets, and an optically black metal sheet 44 with holes, which is arranged to be inside the space defined by said frame and said cover and bottom sheets. Laser cutting, for example, may be employed to cut metal sheet 44 into the desired shape. The glass pieces may be connected by at least one of: glass welding, glass fusing and by using a small and reproducible amount of glue. The requirements for a standard object include long-term stability of its optical properties. In practice this means the standard object should be mechanically and chemically stable and stable against temperature and UV light. It should also be mold and moisture resistant. Cleaning, inspecting, and reproducing the standard should also be easy. All of these requirements are fulfilled by a standard object constructed as shown in FIG. 4.

FIG. 5 illustrates an example computer system 50 capable of supporting at least some embodiments of the present invention. The computer system 50 comprise a processor 51, which may comprise, for example, a single- or multi-core processor wherein a single-core processor comprises one processing core and a multi-core processor comprises more than one processing core. Processor 51 may comprise more than one processor. A processing core may comprise, for example, a Cortex-A8 processing core manufactured by ARM Holdings or a Steamroller processing core produced by Advanced Micro Devices Corporation. Processor 51 may comprise at least one Qualcomm Snapdragon and/or Intel Atom processor.

Processor 51 may comprise at least one application-specific integrated circuit, ASIC. Processor 51 may comprise at least one field-programmable gate array, FPGA. Processor 51 may be means for performing method steps in device 50. Processor 51 may be configured, at least in part by computer instructions, to perform actions.

Computer system 50 also comprises a memory 52. Memory 52 may comprise random-access memory and/or permanent memory. Memory 52 may comprise at least one RAM chip. Memory 52 may comprise solid-state, magnetic, optical and/or holographic memory, for example. Memory 52 may be at least in part accessible to processor 51. Memory 52 may be at least in part comprised in processor 51. The memory 52 comprise computer instructions that processor 51 is configured to execute. When computer instructions configured to cause processor 51 to perform certain actions are stored in memory 52, and device 50 overall is configured to run under the direction of processor 51 using computer instructions from memory 52, processor 51 and/or its at least one processing core may be considered to be configured to perform said certain actions.

Computer system 50 may comprise a data output port or a transmitter 53, and it may also comprise an input port or a receiver 54. Ports 53 and 54 may be configured to transmit and receive, respectively, information in accordance with at least one protocol aimed at data exchange between the components of the inventive apparatus, i.e. the light source, the sphere, the photodetector and a spectroscopy apparatus. Also other external resources may be accessed, such as databases, the internet etc. The ports may be wired or wireless ports.

Computer system 50 may also comprise a near-field communication, NFC, transceiver 55, as an alternative or complement in providing data exchange between the components of the inventive apparatus. The NFC transceiver 55 may support at least one NFC technology, such as NFC, Bluetooth, Wibree or similar technologies.

Additionally, a user interface 56 may be used. The user interface (UI) 56 may comprise at least one of a display, a keyboard and a touchscreen. A user may be able to operate device 50 via UI 56, for example to manage measurements, for example.

Computer system 50 may be arranged to accept at least one external data carrier module 57. Such module may be external memory cards containing configuration or calibration information, for example.

Processor 51 may be furnished with a transmitter arranged to output information from processor 51, via electrical leads internal to device 50, to other devices comprised in computer system 50. Such a transmitter may comprise a serial bus transmitter arranged to, for example, output information via at least one electrical lead to memory 52 for storage therein. Alternatively to a serial bus, the transmitter may comprise a parallel bus transmitter. Likewise processor 51 may comprise a receiver arranged to receive information in processor 51, via electrical leads internal to computer system 50, from other devices comprised in computer system 50. Such a receiver may comprise a serial bus receiver arranged to, for example, receive information via at least one electrical lead from receiver 54 for processing in processor 51. Alternatively to a serial bus, the receiver may comprise a parallel bus receiver.

Computer system 50 may comprise further devices not illustrated in FIG. 5. For example, the computer system 50 may comprise at least one digital camera.

Processor 51, memory 52, transmitter 53, receiver 54, NFC transceiver 55, UI 56 and/or external module 57 may be interconnected by electrical leads internal to device 50 in a multitude of different ways. For example, each of the aforementioned devices may be separately connected to a master bus internal to device 50, to allow for the devices to exchange information. However, as the skilled person will appreciate, this is only one example and depending on the embodiment various ways of interconnecting at least two of the aforementioned devices may be selected without departing from the scope of the present invention.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the preceding description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention.

Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated.

Furthermore, it is to be understood that the use of "a" or "an", that is, a singular form, throughout this document does not exclude a plurality.

INDUSTRIAL APPLICABILITY

At least some embodiments of the present invention find industrial application in increasing precision of spectrometric measurement.

Acronyms List

CIE International Commission on Illumination
NFC Near-Field Communication

The invention claimed is:

1. A method of obtaining a calibrated measurement of a sample using an integrating cavity, comprising:
    obtaining sample spectral information by using the integrating cavity with the sample placed inside the integrating cavity;
    obtaining cavity-characterizing spectral information generated by using the integrating cavity with a standard object;
    obtaining a measurement result from the sample spectral information by employing a mathematical process that takes the cavity-characterizing spectral information as input, and
    obtaining a second cavity-characterizing spectral information and comparing it to the cavity-characterizing spectral information, and responsive to the comparison indicating the second cavity-characterizing spectral information differs from the cavity-characterizing spectral information, using the second cavity-characterizing spectral information in obtaining the measurement result.

2. The method according to claim 1, wherein the cavity-characterizing spectral information is obtained by using the integrating cavity with the standard object placed inside the integrating cavity.

3. The method according to claim 1, wherein the cavity-characterizing spectral information is obtained by using the integrating cavity with the standard object replacing part of an inner surface of the integrating cavity.

4. The method according to claim 1, wherein the cavity-characterizing spectral information is used in to cast spectral information obtained with the sample against the standard object, rather than against the integrating cavity alone.

5. The method according to claim 1, wherein the sample comprises at least one of a solid sample, a liquid sample and a gaseous sample.

6. The method according to claim 1, wherein the sample comprises an agricultural sample.

7. The method according to claim 6, wherein the sample comprises at least one plant seed.

8. The method according to claim 1, wherein the standard object comprises an object with an optically black layer thereon.

9. The method according to claim 8, wherein the object has at least one hole penetrating the optically black layer.

10. The method according to claim 8, wherein the object has plural holes, and wherein the optically black layer covers inside edges of the holes.

11. The method according to claim 9, wherein the object is encased in glass.

12. The method according to claim 11, wherein the glass comprises fused silica or borosilicate glass.

13. The method according to claim 11, wherein the glass is glass welded to enclose the object.

* * * * *